US00PP20579P2

(12) United States Plant Patent
Gerlt

(10) Patent No.: US PP20,579 P2
(45) Date of Patent: Dec. 15, 2009

(54) ***HIBISCUS* PLANT NAMED 'AMERICA IRENE SCOTT'**

(50) Latin Name: *Hibiscus syriacus*
Varietal Denomination: America Irene Scott

(75) Inventor: Sharon Gerlt, Independence, MO (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/229,598

(22) Filed: Aug. 25, 2008

(51) Int. Cl.
*A01H 5/00* (2006.01)

(52) U.S. Cl. ..... Plt./257

(58) Field of Classification Search ..... Plt./257
See application file for complete search history.

*Primary Examiner*—Susan B McCormick Ewoldt
(74) *Attorney, Agent, or Firm*—C. A. Whealy

(57) ABSTRACT

A new and distinct cultivar of *Hibiscus* plant named 'America Irene Scott', characterized by its compact, upright and somewhat outwardly spreading plant habit; freely branching habit; green and yellow variegated leaves; large double pink-colored flowers with numerous petaloids; and good garden performance.

1 Drawing Sheet

Botanical designation: *Hibiscus syriacus.*
Cultivar denomination: 'America Irene Scott'.

BACKGROUND OF THE INVENTION

The present invention relates to a new and distinct cultivar of *Hibiscus,* botanically known as *Hibiscus syriacus,* commercially known as Rose-of-Sharon or Althea, and hereinafter referred to by the name 'America Irene Scott'.

The new *Hibiscus* plant is a naturally-occurring branch mutation of *Hibiscus syriacus* 'Lady Stanley', not patented. The new *Hibiscus* plant was discovered and selected by the Inventor during the summer of 2001 from within a population of plants of the parent in a controlled outdoor nursery environment in Independence, Mo.

Asexual reproduction of the new *Hibiscus* plant by softwood cuttings in a controlled greenhouse environment in Independence, Mo. since July, 2001 has shown that the unique features of this new *Hibiscus* plant are stable and reproduced true to type in successive generations of asexual reproduction.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'America Irene Scott'. These characteristics in combination distinguish 'America Irene Scott' as a new and distinct cultivar of *Hibiscus:*

1. Compact, upright and somewhat outwardly spreading plant habit.
2. Freely branching habit.
3. Green and yellow variegated leaves.
4. Large double pink-colored flowers with numerous petaloids.
5. Good garden performance.

Plants of the new *Hibiscus* can be compared to plants of the parent, 'Lady Stanley'. Plants of the new *Hibiscus* differ from plants of 'Lady Stanley' in the following characteristics:

1. Plants of the new *Hibiscus* are slower growing than and not as vigorous as plants of 'Lady Stanley'.
2. Plants of the new *Hibiscus* have variegated leaves whereas plants of 'Lady Stanley' do not have variegated leaves.

Plants of the new *Hibiscus* can be compared to plants of the *Hibiscus syriacus* 'Purpurea Variegata', not patented. In side-by-side comparisons conducted in Grand Haven, Mich., plants of the new *Hibiscus* differed from plants of 'Purpurea Variegata' primarily in flowering habit as plants of 'Purpurea Variegata' did not produce flowers. In addition, plants of the new *Hibiscus* were slower-growing than and not as vigorous as plants of 'Purpurea Variegata'.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph at the bottom of the sheet is a side perspective view of a typical plant of 'America Irene Scott' grown in a container in an outdoor nursery.

The photograph at the top of the sheet is a close-up view of a typical flower and flower buds of 'America Irene Scott'.

DETAILED BOTANICAL DESCRIPTION

The aforementioned photographs and following observations, measurements and values describe plants grown in Grand Haven, Mich. during the summer in an outdoor nursery and under conditions which closely approximate commercial production. Plants had been growing for three years when the photographs and the description were taken. In the description, color references are made to The Royal Horticultural Society Colour Chart, 1995 Edition, except where general terms of ordinary dictionary significance are used.

Botanical classification: *Hibiscus syriacus* 'America Irene Scott'.

Parentage: Naturally-occurring branch mutation of *Hibiscus syriacus* 'Lady Stanley', not patented.

Propagation:

*Type.*—By softwood cuttings.

*Time to initiate roots.*—About 25 days at 22° C.

*Time to produce a rooted young plant.*—About four months at 22° C.

*Root description.*—Thick.

*Rooting habit.*—Freely branching; dense.

Plant description:

*Plant form and growth habit.*—Perennial shrub. Compact, upright and somewhat outwardly spreading plant habit. Moderately vigorous growth habit.

*Branching habit.*—Freely branching, usually about 37 lateral branches develop per plant after pinching (removal of terminal apices).

*Plant height.*—About 2.5 meters.

*Plant diameter* (*area of spread*).—About 1.25 meters.

Lateral branch description:

*Length.*—About 46 cm.

*Diameter.*—About 5 mm.

*Internode length.*—About 3.7 cm.

*Texture, immature.*—Smooth, glabrous.

*Texture, mature.*—Woody.

*Color, immature.*—Close to 138B.

*Color, mature.*—Close to 197C.

Foliage description:

*Arrangement.*—Alternate, simple.

*Length.*—About 7 cm.

*Width.*—About 4 cm.

*Shape.*—Rhomboidal, tri-lobed.

*Apex.*—Acute.

*Base.*—Cuneate.

*Margin.*—Crenate; tri-lobed.

*Texture, upper and lower surfaces.*—Smooth, glabrous.

*Venation pattern.*—Pinnate.

*Color.*—Developing leaves, upper and lower surfaces: Close to 137C; towards the margins, close to 160C. Fully expanded leaves, upper surface: Close to 138A; towards the margins, close to 160B to 160C; venation, close to 138B. Fully expanded leaves, lower surface: Close to 138B; towards the margins, close to 160C; venation, close to 138B.

*Petiole.*—Length: About 6 mm. Diameter: About 2 mm. Texture, upper and lower surfaces: Smooth, glabrous. Color, upper and lower surfaces: Close to 138A to 138B.

Flower description:

*Flower appearance/arrangement.*—Double rotate flowers; terminal and axillary. Freely flowering habit with usually about 15 flowers developing per lateral branch. Flowers face upright to outwardly.

*Flower longevity.*—Flowers last for about one to two days on the plant. Flowers not persistent.

*Natural flowering season.*—Plants typically flower from July to September in Michigan.

*Flower diameter.*—About 6.5 cm.

*Flower depth.*—About 3 cm.

*Flower bud.*—Length: About 1 cm. Diameter: About 9 mm. Shape: Ovate. Color: Close to 138B.

*Petals.*—Arrangement/quantity: Single whorl of five petals; petals imbricate. Length: About 3.5 cm. Width: About 2.5 cm. Shape: Broadly elliptic to obovate. Apex: Obtuse. Base: Attenuate. Margin: Entire; undulate. Texture, upper and lower surfaces: Smooth, glabrous. Color: When opening and fully opened, upper surface: Close to 62D; towards the base and venation, close to 60A. Color fades towards 155D with development. When opening and fully opened, lower surface: Close to 62D.

*Petaloids.*—Arrangement/quantity: About 46 petaloids in several whorls; petaloids imbricate. Length: Variable depending on stage of development, about 0.5 cm to 2.5 cm. Width: Variable depending on stage of development, about 0.2 cm to 1.5 cm. Shape: Obovate to spatulate. Apex: Obtuse. Base: Attenuate. Margin: Entire; undulate. Texture, upper and lower surfaces: Smooth, glabrous. Color: When opening, upper and lower surfaces: Close to 62D. Fully opened, upper and lower surfaces: Close to 62D; towards the base and venation, close to 60A.

*Sepals.*—Appearance: Five sepals fused into a star-shaped calyx. Length: About 1.7 cm. Width: About 8 mm. Shape: Roughly ovate. Apex: Acute. Margin: Entire. Texture, upper and lower surfaces: Smooth, glabrous. Color, immature and mature, upper and lower surfaces: Close to 138B; towards the margins, close to 160B to 160C.

*Peduncles.*—Length: About 1.4 cm. Diameter: About 3 mm. Strength: Strong, flexible. Texture: Smooth, glabrous. Angle: About 40° from the stem. Color: Close to 138B.

*Reproductive organs.*—None observed, all transformed into petaloids.

*Seeds/fruits.*—Seed and fruit development have not been observed on plants of the new *Hibiscus* plant.

Garden performance: Plants of the new *Hibiscus* have been observed to have excellent garden performance and to tolerate rain, wind and temperatures ranging from about −20° C. to about 35° C.

Pathogen/pest resistance: Plants of the new *Hibiscus* have not been shown to be resistant to pathogens and pests common to *Hibiscus*.

It is claimed:

1. A new and distinct *Hibiscus* plant named 'America Irene Scott' as illustrated and described.

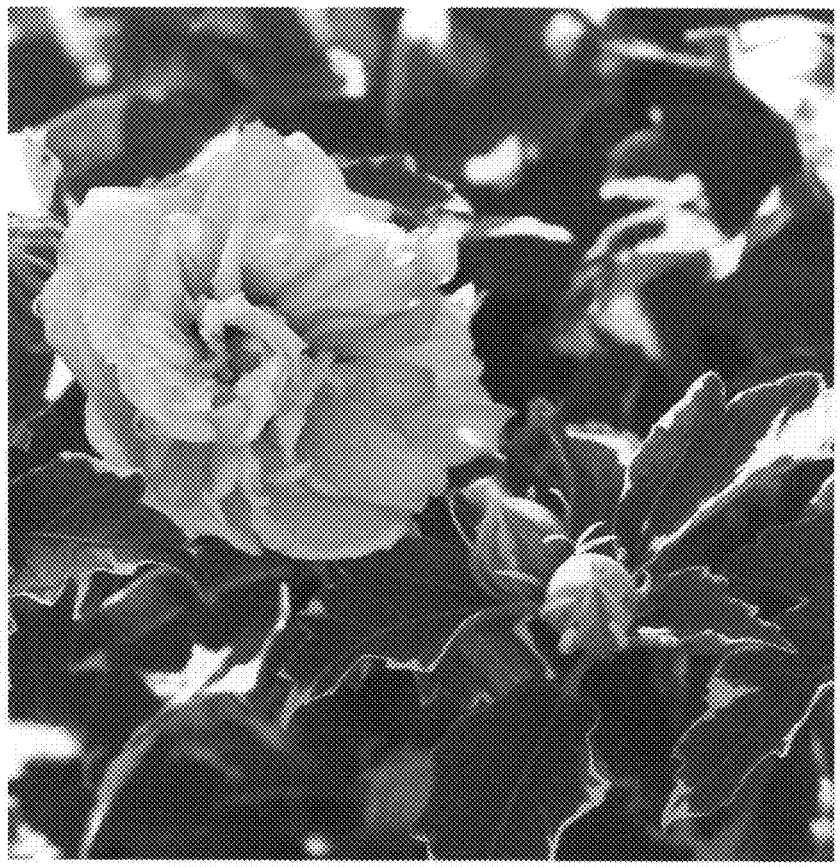
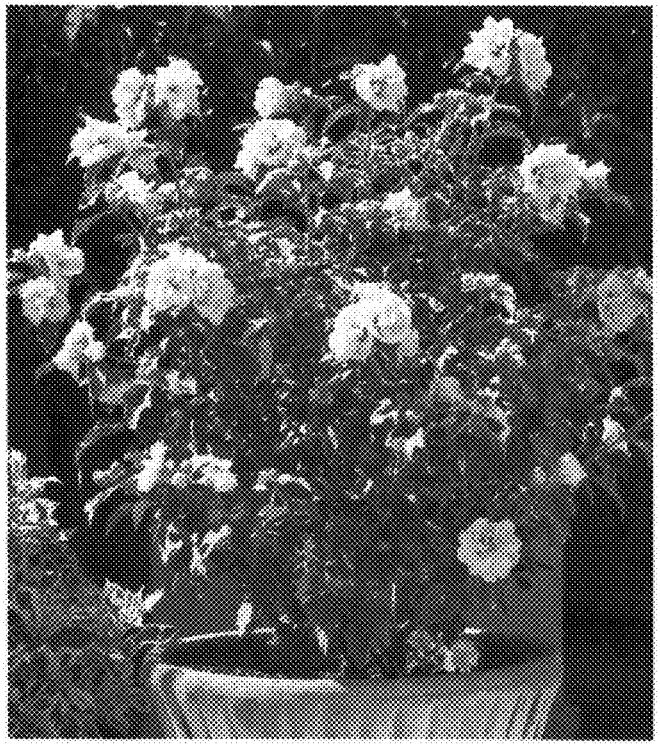

* * * * *